United States Patent
Tran et al.

(10) Patent No.: US 6,248,986 B1
(45) Date of Patent: Jun. 19, 2001

(54) PREFERENTIAL HEATING OF MATERIALS BY USE OF NON-IONIZING ELECTROMAGNETIC RADIATION

(75) Inventors: Van Nguyen Tran, Bundoora; Christopher Chia Shyong Pan, West Footscray; David Lee Carew, St. Albans, all of (AU)

(73) Assignee: Amcor Packaging (Australia) Pty. Ltd. (AU)

( * ) Notice: Subject to any disclaimer, the term of this patent is extended or adjusted under 35 U.S.C. 154(b) by 0 days.

(21) Appl. No.: 09/445,354
(22) PCT Filed: Jun. 11, 1998
(86) PCT No.: PCT/AU98/00448
  § 371 Date: Feb. 14, 2000
  § 102(e) Date: Feb. 14, 2000
(87) PCT Pub. No.: WO98/57523
  PCT Pub. Date: Dec. 17, 1998

(30) Foreign Application Priority Data

Jun. 11, 1997 (AU) .................................................. PO 7287

(51) Int. Cl.⁷ .............................. H05B 6/64; B65B 55/08
(52) U.S. Cl. .......................... 219/679; 219/702; 219/715; 422/21; 426/241
(58) Field of Search ...................... 219/679, 702, 219/715, 678; 422/21; 426/234, 241, 243; 99/DIG. 14, 451

(56) References Cited

U.S. PATENT DOCUMENTS

| 4,434,341 | * | 2/1984 | Busby ................................... 219/748 |
| 4,554,347 | | 11/1985 | Hawkes, Jr. . |
| 4,956,530 | * | 9/1990 | Koch ..................................... 219/700 |
| 5,144,146 | | 9/1992 | Wekhof . |
| 5,166,484 | | 11/1992 | Young et al. . |
| 5,364,645 | | 11/1994 | Lagunas-Solar et al. . |
| 5,440,104 | | 8/1995 | Koch et al. . |

FOREIGN PATENT DOCUMENTS

| 2712448 | 9/1978 | (DE) . |
| 5-103610 | 4/1993 | (JP) . |
| WO 89/10069 | 11/1989 | (WO) . |
| WO 96/25048 | 8/1996 | (WO) . |

* cited by examiner

Primary Examiner—Philip H. Leung
(74) Attorney, Agent, or Firm—Killworth, Gottman, Hagan & Schaeff, LLP

(57) ABSTRACT

Method and apparatus for preferential heating of a material are based on exposing the material to high intensity, pulsed, non-ionizing electromagnetic radiation. The method can destroy microorganisms, sterilize packaging, or sterilize moist food. An embodiment uses microwave radiation with pulse duration of less than 0.1 second with an average power of at least 1 kW to sterilize open-ended metal can prior to packaging.

10 Claims, 1 Drawing Sheet

PREFERENTIAL HEATING OF MATERIALS BY USE OF NON-IONIZING ELECTROMAGNETIC RADIATION

BACKGROUND OF THE INVENTION

The present invention relates to preferential heating of materials by non-ionising electromagnetic radiation.

The term "non-ionising electromagnetic radiation" is understood to include, by way of example, microwave radiation and radio wave radiation.

One particular, although by no means exclusive, use of the present invention is to preferentially heat micro-organisms to temperatures that destroy the micro-organisms.

This use of the present invention has a large number of applications.

One application is the medical industry in which the invention may be used, by way of example, to sterilise pharmaceuticals, packages for pharmaceuticals, and surgical and other equipment and implements.

Another application, which is of particular interest to the applicant, is the food processing industry.

The term "food processing industry" is understood to cover industry involved in preparing and packaging food products, including solid and liquid food products.

It is a critical requirement of the food processing industry:

(i) to sterilise food products after the food products have been packaged; or (ii) to prepare and thereafter package food products under sterile conditions.

One example of the first category is the widely used method of packaging beverages, such as beer, which comprises pasteurising the beverages. Typically, suitable packaging (such as metal or glass containers) is filled with the beverages, the packaging is sealed, and the packaged beverages are thereafter heated at a temperature of 65–70° C. for 15 minutes. This method, whilst effective, has a number of disadvantages including substantial capital and operating costs.

Another example of the first category is the known method of sterilising spices. Typically, suitable packaging is filled with spices, the packaging is sealed, and thereafter ethylene oxide is permeated through the packaging at high pressure and contacts and destroys micro-organisms on the spices. While ethylene oxide is an efficient means of destroying bacterial spores and other micro-organisms carried by the spices, it is toxic and therefore removal of residual ethylene oxide to low levels is critical. Inevitably, this involves careful control of the method which in turn increases operating costs.

An example of the second category is packaging beverages under aseptic conditions.

Typically, beverages are prepared and conveyed to a filling station under sterile conditions, the filling equipment is maintained under sterile conditions, packaging is sterilised and transported to the filling station under sterile conditions, and the beverages are filled into the packaging and the packaging is sealed under sterile conditions.

An important factor in aseptic packaging of food products is the sterilisation of the packaging.

Known technologies for sterilising packaging in the food processing industry include:

(i) chemical sterilisation, such as hydrogen peroxide and chlorine;

(ii) UV radiation;

(iii) gamma radiation; and (iv) steam sterilisation.

There are advantages and disadvantages with each option and the suitability of these (and other) technologies in any given situation depends on the packaging, the food product, and the food preparation.

SUMMARY OF THE INVENTION

A particular object of the present invention is to provide an alternative to known technologies for sterilising packaging for the food processing industry.

A more general object of the present invention is to provide an alternative to known sterilisation technologies in the Food processing industry and other industries.

According to the present invention there is provided a method of preferential heating of a material which comprises exposing the material to high intensity, pulsed, non-ionising electromagnetic radiation.

The present invention is based on experimental work carried out with high intensity, pulsed, microwave radiation.

It was found in the experimental work that high intensity, pulsed, microwave radiation is a particularly effective means of destroying micro-organisms. It is believed that the high intensity, pulsed microwave radiation caused a substantial net increase in energy in the micro-organisms which resulted in a sudden temperature increase in the micro-organisms that destroyed the micro-organisms.

It was also found in the experimental work that high intensity, pulsed microwave radiation could destroy micro-organisms without heating substantially the surrounding environment that was also exposed to the radiation.

The parameters that are important to this preferential heating of micro-organisms include the high intensity, pulsed energy, the microwave absorptivity of the surrounding environment, and the size of micro-organisms exposed to the radiation. With regard to the third factor, generally, the rate of heat build-up in a material is slower with larger size of an object that comprises the material. In general terms, where the size of 2 objects is the same, the relative absorptivity of the objects will determine the extent of preferential heating, and where the absorptivity of the objects is the same, the relative size of the objects will determine the extent of preferential heating.

In the context of the food processing industry preferential heating with non-ionising electromagnetic radiation, such as microwave radiation, makes it possible to sterilise packaging by destroying micro-organisms on the packaging without causing significant heating of the packaging that would alter adversely the chemical or other properties of the packaging.

Again, in the context of the food processing industry, preferential heating with non-ionising electromagnetic radiation makes it possible to sterilise moist food prior to or after the food has been packaged. In this context, it is within the scope of the present invention to focus high intensity, pulsed non-ionising electromagnetic radiation onto the head spaces of sealed beverage containers and jam jars to sterilise the head spaces.

The term "moist food" is understood to cover food having a water activity (ie. the ratio of vapour pressure of water in food to the vapour pressure of water) of less than 1.0.

Again, in the context of the food processing industry, the present invention is not limited to situations in which the food products being packaged are "moist".

There is considerable flexibility in the selection of the characteristics of non-ionising electromagnetic radiation (such as power, intensity, and wavelength) and the parameters that define the pulses (such as pulse duration, pulse frequency, pulse profile, duty cycle and average power) to achieve effective destruction of micro-organisms. An important consequence of the flexibility is that it is possible to select operating parameters for the high intensity, pulsed, non-ionising electromagnetic radiation that suit the characteristics of particular food products and packaging.

The intensity/time pulse train of the pulses may be any suitable profile. It is preferred that the pulse train be rectangular.

Preferably the pulse duration is less than 1 second.

More preferably the pulse duration is less than 0.1 seconds.

More preferably the pulse duration is less than 0.01 seconds.

In general terms it is preferred that the pulse duration be selected so that there is insufficient exposure to cause significant heating of dry materials, such as packaging materials.

Preferably the average power of the microwaves is at least 0.1 kW.

More preferably the average power is at least 1 kW.

More preferably the average power is at least 5 kW.

The term "average power" is understood to mean the product of the peak power and the duty cycle.

The term "peak power" is understood to mean the maximum power of a pulse.

The term "duty cycle" is understood to mean the time span of a pulse divided by the sum of the pulse time span and the time between pulses.

Preferably the peak power of the radiation is at least 1 kW.

More preferably the peak power of the radiation is at least 3 kW.

More preferably the peak power is at least 30 kW.

Preferably the pulse frequency is less than 100 pulses per second.

More preferably the pulse frequency is less than 50 pulses per second.

It is preferred particularly that the pulse frequency be less than 30 pulses per second.

According to the present invention there is provided an apparatus for preferentially heating a material which comprises a means for generating high intensity, pulsed, non-ionising electromagnetic radiation.

Preferably the apparatus comprises a means for directing the radiation onto the material.

More preferably the direction means comprises a means for focusing the radiation.

As described above, a preferred, although by no means exclusive, application of the present invention is to destroy micro-organisms by preferential heating.

In this application, it is preferred that the apparatus further comprises a means for directing high intensity, pulsed, microwave radiation into a sterilisation region.

The sterilisation region may be any region that is required to be a sterile environment.

By way of example, the sterilisation region may be a chamber for sterilising empty packaging for food products.

In this example, the apparatus further comprises a transport means, such as a conveyor belt, for moving the empty packaging into and from the chamber, whereby the packaging is exposed to high intensity, pulsed, radiation in the chamber.

BRIEF DESCRIPTION OF THE DRAWING

The present invention is described further by way of example with reference to the accompanying drawing FIG. 1, which is a schematic diagram of a preferred embodiment of an apparatus for sterilising packaging for the food processing industry prior to the packaging being filled with a food product and sealed.

DETAILED DESCRIPTION OF THE INVENTION

Figure 1:
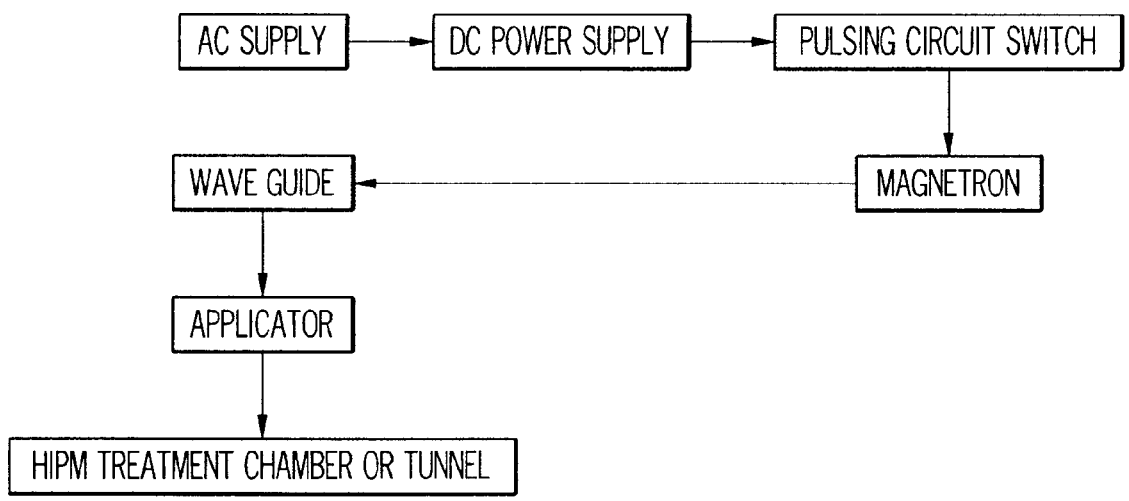

As indicated above, the present invention is directed particularly, although by no means exclusively, to the use of high intensity, pulsed, non-ionising electromagnetic radiation, such as microwave radiation, to destroy micro-organisms.

It is understood that the following description in relation to sterilising unfilled, open packaging for the food processing industry is by way of example only.

With reference to the FIGURE, alternating current electricity is supplied to a DC power supply, which may include a transformer, and then to a pulsing circuit or switch to produce pulses in a required intensity duty cycle. The alternating current electricity may be supplied from any suitable source, such as 60 Hz AC, 600 Hz AC, 3 phase AC, and single phase AC.

The pulses are supplied to a microwave active device, such as a magnetron, which produces pulses of high intensity microwave radiation at a prescribed duty cycle.

Thereafter, the high intensity, pulsed, microwave radiation is transferred via a wave guide into an applicator to a treatment chamber or tunnel.

In a suitable form of treatment chamber or tunnel (not shown), the packaging, such as open-ended metal cans, is arranged on a conveyor belt which transports the packaging, in upright positions, through the chamber or tunnel so that the packaging is exposed to multiple pulses of high intensity, pulsed, microwave radiation which heat micro-organisms on the packaging to temperatures that destroy the microorganisms.

In this connection, it is noted that in situations where the packaging is metal cans, since metals reflect microwaves it is important to ensure that the relative positions of the applicator and the cans are selected so that the high intensity, pulsed, microwave radiation is directed through the open ends into the interior of the cans.

The preferred embodiment of the present invention shown in the FIGURE has considerable advantages over known technologies of chemical sterilisation, UV radiation, gamma radiation, and steam sterilisation for sterilising packaging. By way of example, the capital and operating costs are relatively low compared to each of the known technologies. In addition, there is no risk of leaving residual chemicals on the packaging—which is an issue with chemical sterilisation, particularly when the chemicals concerned, such as hydrogen peroxide, are poisonous. Moreover, the use of non-ionising electromagnetic radiation makes it possible to avoid chemical changes to packaging—which is an issue with UV and gamma radiation. For example, it is possible to destroy micro-organisms without generating levels of heat in the packaging that could alter the chemical properties of the packaging—which is an issue with steam sterilisation. Furthermore, the penetrating power of high intensity microwave radiation is such that there is a high level of assurance that regions of non-metallic packaging will not avoid exposure—which is an issue with UV radiation Furthermore, the preferred embodiment is adapted to high speed sterilisation and, therefore, is well-suited to high-throughput applications that are often found in industries such as the food processing industry.

The above advantages of the preferred embodiment are also generally applicable to the use of high intensity, pulsed, microwave radiation in other situations in the food processing industry and in other applications.

In a series of experiments 8 kW DC power was supplied to a pulsing switch which produced a pulsed microwave output of 3 kW at a duty cycle of 25% with 0.025 seconds long pulses and 0.075 seconds between pulses which is a pulse rate of 10 pulses per second.

The pulsed microwave output was produced by a S-band magnetron operating at 2.460 GHz.

The microwaves were focussed onto yeast spores on a 50 micron thick microwave-transparent plastic film. The density of the yeast spores was estimated to be between $10^8$ and $10^{10}/cm^2$. The yeast spores were exposed for a total time of 2–5 seconds.

A quantitative assessment of the results concludes that the spores were totally destroyed and that there was minimal heating of the support substrate. The experiment established that the invention could sterilise a surface of a material, such as a packaging material, with minimal thermal effect on the material.

Many modifications may be made to the preferred embodiment described above without departing from the spirit and scope of the present invention.

By way of example, whilst the preferred embodiment described in relation to the FIGURE includes a pulsing switch, it can readily be appreciated that the present invention is not so limited and extends to any other suitable pulsing network.

Furthermore, whilst the preferred embodiment includes a magnetron, it can readily be appreciated that the present invention is not so limited and extends to any other suitable means for generating microwaves. Possible alternatives include solid state devices, klyptrons and gyratrons.

What is claimed is:

1. A method of destroying micro-organisms which comprises exposing the micro-organisms to pulsed microwave radiation that has a pulse duration of less than 1 second, a pulse frequency of less than 100 pulses per second, an average power of at least 1 kw, and a peak power of at least 3 kW which destroys the micro-organisms without substantial heating of the surrounding environment that is also exposed to the radiation.

2. The method defined in claim 1 wherein the pulse duration is less than 0.1 seconds.

3. The method defined in claim 2 wherein the pulse duration is less than 0.01 seconds.

4. The method defined in claim 1 wherein the average power is at least 5 kW.

5. The method defined in claim 1 wherein the peak power is at least 30 kW.

6. The method defined in claim 1 wherein the pulse frequency is less than 50 pulses per second.

7. The method defined in claim 6 wherein the pulse frequency is less than 30 pulses per second.

8. The method defined in claim 1 wherein said exposing step comprises generating pulsed microwave radiation and thereafter focusing the radiation onto a target area to expose micro-organisms in the target area.

9. A method of sterilising packaging which comprises exposing the packaging to pulsed microwave radiation that has a pulse duration of less than 1 second, a pulse frequency of less than 100 pulses per second, an average power of the least 1 kW, and a peak power of at least 3 kW which destroys micro-organisms without causing heating of the packaging that alters adversely the chemical on other properties of the packaging.

10. A method of sterilising moist food prior to or after the food has been packaged which comprises exposing the packaging to pulsed microwave radiation that has a pulse duration of less than 1 second, a pulse frequency of less than 100 pulses per second, an average power of at least 1 kW, and a peak power of at least 3 kW which destroys microorganisms without causing heating of the packaging or any food contained in the packaging that alters adversely the chemical or other properties of the packaging or the food.

* * * * *